(12) United States Patent
Garrison

(10) Patent No.: US 10,179,353 B2
(45) Date of Patent: Jan. 15, 2019

(54) SPRAYING APPARATUS FOR CLEANING CARBOYS AND ASSOCIATED METHODS THEREOF

(71) Applicant: Richard Lee Garrison, Salisbury, NC (US)

(72) Inventor: Richard Lee Garrison, Salisbury, NC (US)

( * ) Notice: Subject to any disclaimer, the term of this patent is extended or adjusted under 35 U.S.C. 154(b) by 61 days.

(21) Appl. No.: 14/829,857

(22) Filed: Aug. 19, 2015

(65) Prior Publication Data

US 2017/0050225 A1    Feb. 23, 2017

(51) Int. Cl.
*B08B 9/08* (2006.01)
*A61L 2/18* (2006.01)
*C12C 13/10* (2006.01)
*B08B 3/02* (2006.01)
*B08B 9/093* (2006.01)

(52) U.S. Cl.
CPC .............. *B08B 9/0813* (2013.01); *A61L 2/18* (2013.01); *B08B 3/02* (2013.01); *B08B 9/093* (2013.01); *C12C 13/10* (2013.01)

(58) Field of Classification Search
None
See application file for complete search history.

(56) References Cited

U.S. PATENT DOCUMENTS 4,805,650 A * 2/1989 Yasui ............... B08B 9/093
134/167 R
2005/0045751 A1* 3/2005 Nance ............... B05B 15/061
239/587.1

FOREIGN PATENT DOCUMENTS

EP    2008723    * 12/2008

* cited by examiner

*Primary Examiner* — Michael E Barr
*Assistant Examiner* — Jason P Riggleman
(74) *Attorney, Agent, or Firm* — Ben Schroeder Law, PLLC

(57) ABSTRACT

A spraying apparatus is disclosed that allows the interior of a carboy that has been used to make beer. The spraying apparatus comprises a main arm, an articulating arm, a hose, and a controller, the main arm being operationally connected to the articulating arm, and the controller controlling the amount of articulation from the articulating arm. The device is able to reach areas in the carboys that are hard to reach with brushes.

20 Claims, 4 Drawing Sheets

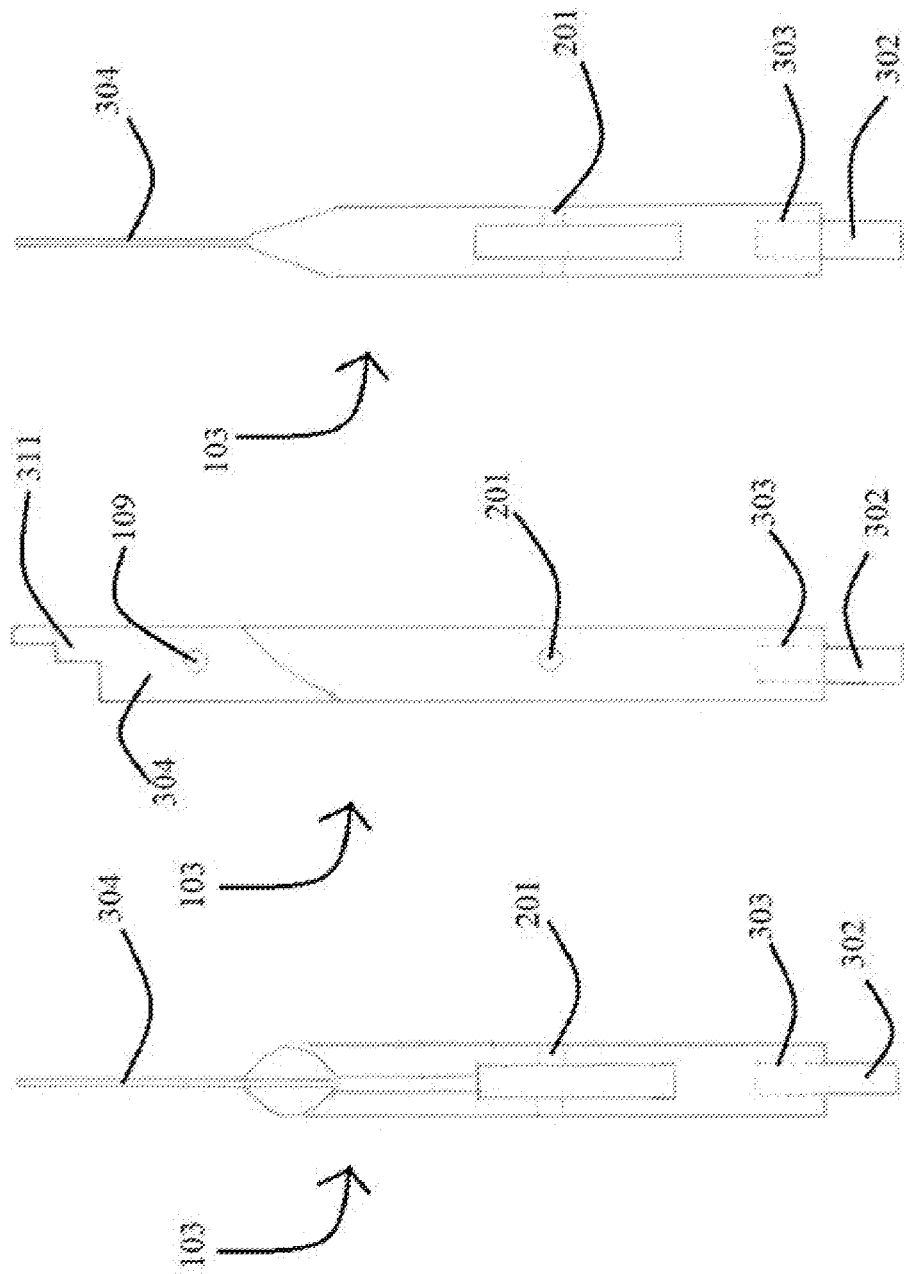

SPRAYING APPARATUS FOR CLEANING CARBOYS AND ASSOCIATED METHODS THEREOF

FIELD OF THE INVENTION

The present invention relates to a spraying apparatus that allows the interior of a carboy that has been used to make beer to be cleaned. The spraying apparatus comprises a main arm, an articulating arm, a hose, and a controller, the main arm being operationally connected to the articulating arm and the controller controlling the amount of articulation from the articulating arm. The device is able to reach areas in the carboys that are hard to reach with brushes.

BACKGROUND OF THE INVENTION

Beer has been around for millennia. The ancient Egyptians and people from Mesopotamia were brewing beer since at least the fifth millennium BC. In the $7^{th}$ century, beer was made in monasteries throughout Europe and the industrial production of beer started in the $19^{th}$ century where it has continued until today. In the United States, beer production generates more than $100 billion in revenue. The market share for craft beer revenue in the United States has been growing and in 2014, it was estimated to be about ⅕ of the total U.S. beer revenue.

The combination of contract brewers, microbreweries, brew pubs and regional breweries brewed slightly more than 5,000,000 barrels of beer in the United States in 2004, wherein in 2014, the combination of these amounted to over 20,000,000 gallons of beer. Thus, small beer brewing has been increasing as a share of the total beer industry.

One big potential problem with the production of beer is contamination that may be caused by bacteria. In many cases, bacteria that are present in a brew may grow faster than the yeast that ferments the beer, leading to contaminated beer. Two of the more common bacteria that contaminate beer are *pediococcus* and/or *lactobacillus* bacteria. Although one may be able to still drink the beer, these bacteria often provide the beer with a stench that reminds some of rotten cabbage and/or a smelly cheese. Other bacteria that are more dangerous include the various strains of *Escherichia, Campylobacter, Listeria, Clostridium, Brettanomyces, Acetobacter*, and/or *Staphylococcus*. If any of these various strains of bacteria infect beer, it can result in severe symptoms for the drinker. Generally, only a few of these bacteria can survive the fomentation conditions to make beer. Nevertheless, to reduce the risk of bacterial contamination, a thorough cleaning of the beer fermenting apparatus is necessary.

The big industrial breweries have established brewing standards that allow for cleaning of their equipment by the use of mechanical means such as scrubbers, harsh detergents, and solvents. Smaller beer breweries and home brewers often lack the initial capital resources to employ some of these expensive cleaning implements. Moreover, small batch brewers also often wish to avoid the use of environmentally questionable cleaners that the industrial beer producers use. Home brewers tend to have even less capital available for cleaning than do the beer breweries so they tend to use low tech cleaning such as the use of scrubbing brushes, soap, and water.

Generally, when one home brews (or brews on a small scale), one will use carboys or some other suitable container that allows one to foment beer. In carboys, krausen, which is the foamy and bubbly head that forms on the top of beer during primary fermentation may bubble up sufficiently so that the wort may remain stuck on the top inner surface of the carboy. If one employs brushes to clean the carboy after fermentation, cleaning the upper inner surface of the carboy often proves to be problematic as the brush cannot easily pass through the hole of the carboy and then reach the upper inner surface of the carboy. Accordingly, when the carboy is employed again for the next beer fermentation, the carboy may not be sufficiently clean, leading to some of the problems discussed above.

It is with these drawbacks in mind that the instant invention was developed.

BRIEF SUMMARY OF THE INVENTION

The present invention relates to an apparatus for cleaning the inside of containers. In an embodiment the present invention relates to an apparatus that can be used to clean the inside of containers that make beer. In one embodiment, the present invention relates to an apparatus that can clean the inside of carboys. In an embodiment, the apparatus of the present invention contains an articulating arm that allows the cleaning of containers that have hard to reach areas.

BRIEF DESCRIPTION OF THE SEVERAL VIEWS OF THE DRAWINGS

FIG. 3A, FIG. 3B, and FIG. 3C show the front view (FIG. 3A), the side view (FIG. 3B) and back view (FIG. 3C) of a part of the articulating arm, respectively.

DETAILED DESCRIPTION OF THE INVENTION

The present invention relates to an apparatus for cleaning the inside of containers. In an embodiment, the present invention relates to an apparatus that can be used to clean the inside of containers that make beer. In one embodiment, the present invention relates to an apparatus that can clean the inside of carboys. In an embodiment, the apparatus of the present invention contains an articulating arm that allows the cleaning of containers that have hard to reach areas.

The invention will now be described with reference to the figures. It should be understood that this description is in no way to be limiting but is described to explain embodiments of the invention.

Figure 1:
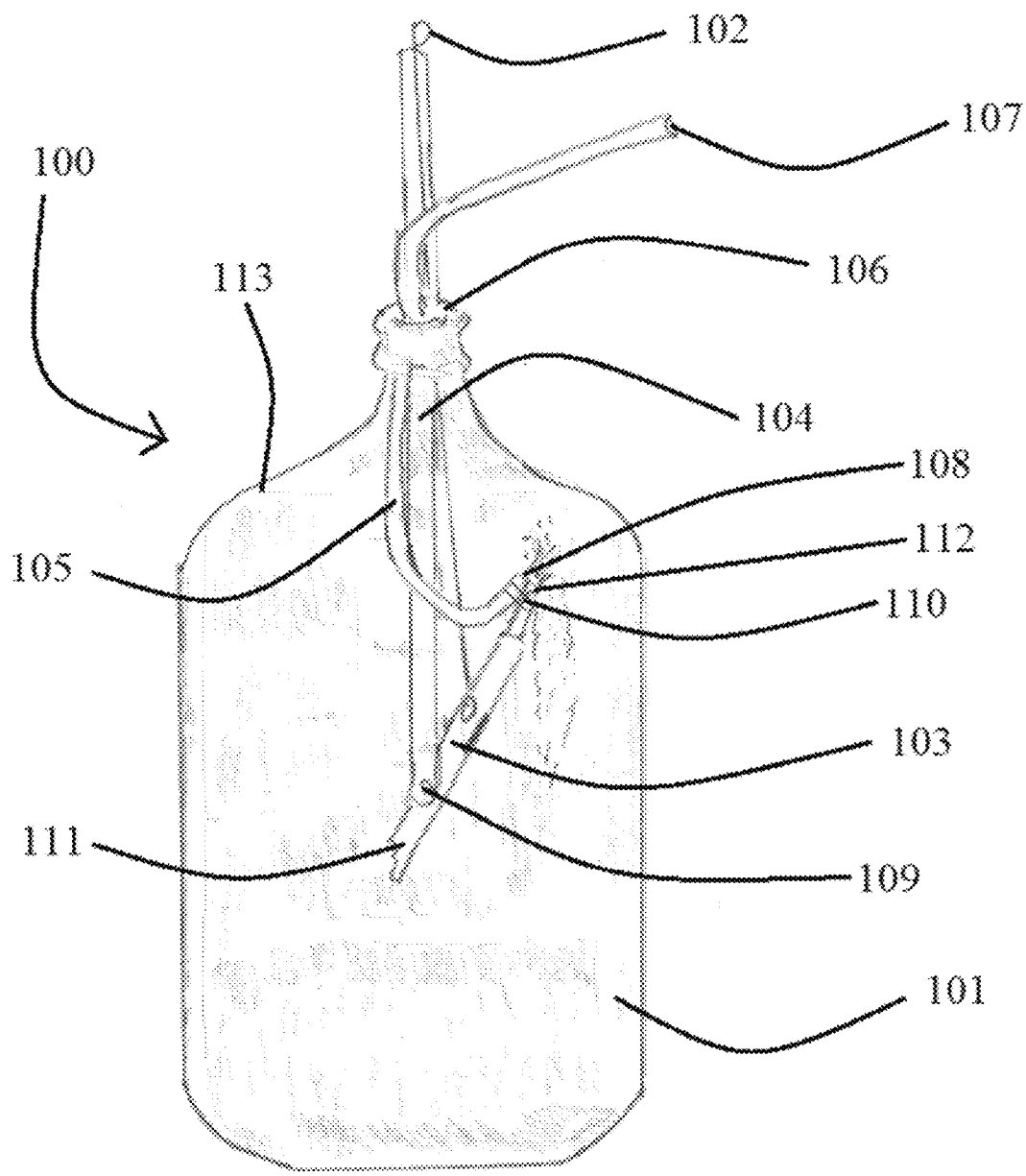
FIG. 1 shows a perspective drawing of a carboy with the cleaning apparatus of the present invention inside the carboy.

As can be seen in FIG. 1, a carboy and apparatus combination 100 is seen with the apparatus inserted into the opening 106 of the carboy 101. The cleaning apparatus comprises four main parts, 1) a controller 102, 2) an articulating arm 103, 3) a main arm 104, and 4) a hose 105. The hose 105 comprises a proximal end 107 and a distal end 108. Between the articulating arm 103 and the main arm 104 is a joint 109, which allows the articulating arm 103 to articulate to any of a plurality of bent states off of the main arm 104. The articulating arm 103 comprises a near end 111, of the articulating arm and a far end 112 of the articulating arm. Clamp 110 keeps the distal end 108 of the hose 105 in close proximity to the far end 112 of the articulating arm 103. The apparatus is designed in such a way that allows one to clean the upper inner surface 113 of the carboy 101.

Figure 2A:
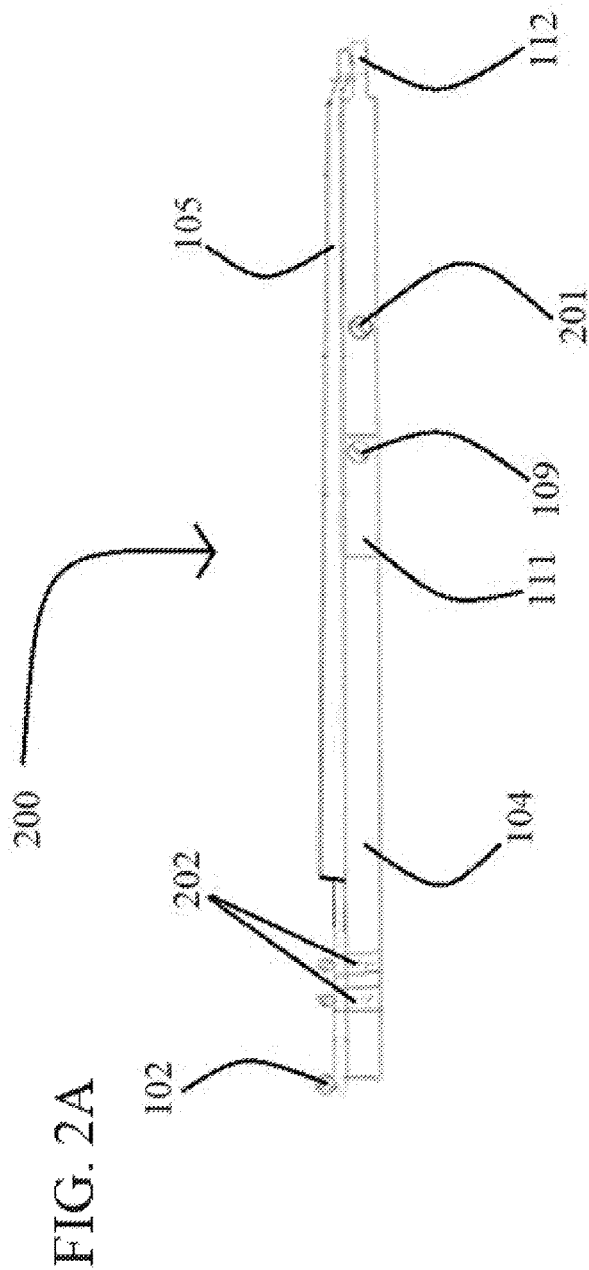
FIG. 2A and FIG. 2B show the cleaning apparatus of the invention in its folly extended state (FIG. 2A) and in a bent state (FIG. 2B).

The cleaning apparatus is inserted into the carboy opening 106 in its extended or straight state (see FIG. 2A). The cleaning apparatus works by attaching a water source to the proximal, end 107 of the hose 105. The water travels through the hose 105 and is expelled on the distal end 108 of the hose 105. By manipulating controller 102, one is able to articulate the articulating arm 103 at joint 109 to any of a plurality of positions including the position shown in FIG. 1. Articulating arm 103 is able to attain any of a plurality of positions, such as positions that are between an angle of about 0° to a position that has an angle about 180° relative to die main arm 104. Because hose 105 is flexible and distal end 108 of hose 105 is clamped by clamp 110 at far end 112 of the articulating arm 103, the hose 105 will shoot water from distal cod 108 in the direction that articulating arm 103 attains when articulating arm 103 articulates relative to main arm 104. Thus, by manipulating controller 102, one can clean the entire inner surface of carboy 101 including positions that are typically difficult to reach for brushes including upper inner surface 113.

Although clamps (such as hose clamps) are shown in some of the figures, it should be understood that other means of keeping the hose adjacent the main arm or articulating arm are contemplated and therefore within the scope of the invention. For example, adhesives may be used, or hooks or rings may be used, or other methods may be employed such as nylon cable ties or string.

In an embodiment, the articulating arm 103 should be of a length (from the near end 111 to a far end 112) that allows articulating arm 103 to go from any position with angle of about 0° to angle of about 180°. If the articulating arm 103 is too long (e.g., the length of articulating arm is longer than approximately a length that is about equal to the radius of the cylindrical carboy), once the apparatus 200 enters the carboy, the articulating arm 103 would not be able to attain all positions between about 0° and 180° relative to the main arm 104 because the inner surface of the carboy 101 would prevent the articulating arm 103 from being articulable, it should be noted that this length is approximate because the articulating arm's position in the carboy can be manipulated somewhat so that lengths of the articulating arm 103 that are slightly longer than the radius of the cylindrical carboy can accommodate all positions between about 0° and 180° relative to the main arm 104 (e.g., by having the main arm 104 enter the opening 106 at an angle).

Figure 2B:
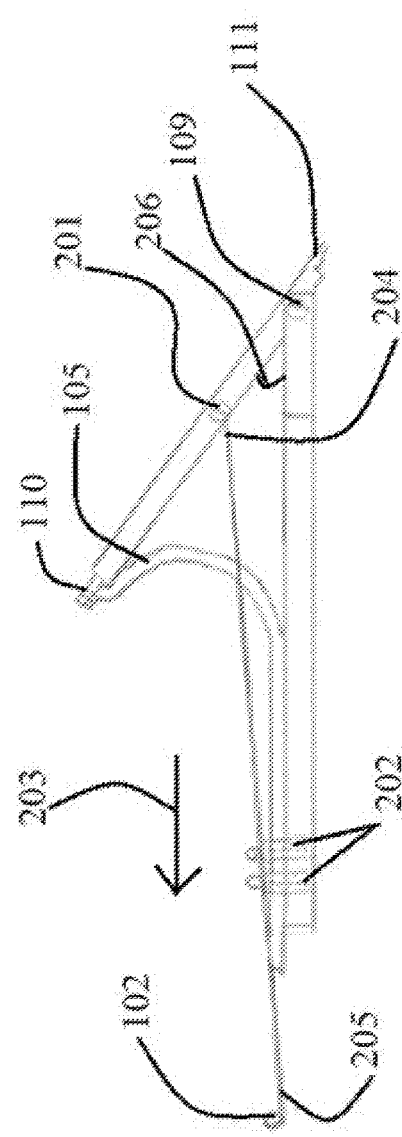

FIGS. 2A and 2B show the apparatus 200 in an extended, or straight state (FIG. 2A) or in a bent state (FIG. 2B). In one embodiment (and as shown in FIGS. 2A and 2B) the controller 102 may have a loop at the end of the controller 102 that is outside of the carboy (see FIG. 1). This may allow a user of the apparatus 200 to use a finger that can be inserted into said loop to manipulate the controller 102.

As can be seen in FIG. 2A, there are clamps 202 that hold, controller 102 in place so that it stays principally parallel to main arm 104. In one embodiment, clamps 202 also may hold hose 105 so that it stays in a position that is substantially adjacent to main arm 104 at the proximal end 107 of the hose 105. Moreover, the presence of clamp 110 allows the hose 105 to stay substantially adjacent to articulating arm 103 at distal end 108 of hose 105. Because hose 105 is flexible, this allows the passage of water through the hose 105 in such, a way that any interior part of the carboy 101 can be washed.

In FIG. 2A and FIG. 2B there is shown a connection point 201 for die distant end 204 of controller 102 that allows one to articulate articulating arm 103. By pulling the controller 102 at the proximate end 205 of controller 102 in a direction that is shown by arrow 203, the articulating arm pivots around joint 109 so that angle 206 can attain angles between about 0° and 180°. When controller 102 moves in the direction that is shown by arrow 203, angle 206 gets smaller and when controller 102 moves in a direction opposite that shown by arrow 203, angle 206 becomes larger. In one embodiment, the connection point is a point that is about hallway between the near end and the for end of the articulating arm.

In an embodiment, and as shown in FIG. 2B, near end 111 of the articulating arm 103 contains a step-like feature that prevents the articulating arm from attaining a position wherein angle 206 is more than 180°.

FIGS. 3A, 3B, and 3C show the front view, the side view and back view of a part of the articulating arm 103, respectively. In FIG. 3B, one should note that at the near end of the articulating arm, there appears a step-like feature 311 that when the articulating arm 103 is in the extended or straight state, this step-like feature 311 prevents the articulating arm from going beyond 180°. FIG. 4B shows the accompanying step-like receiving feature 411 that is designed to accommodate the step like feature 311 of the articulating arm 103. Joint 109 is in a position that, allows the articulating arm to articulate and joint 109 is in a position that allows a screw of a nut to go through it and also through the corresponding hole 409 in FIG. 4B. The connection point 201 can be seen in all of FIGS. 3A, 3B, and 3C and in one embodiment, the connection point may have a threaded hole drilled through the articulating arm from one side to the next (best seen in FIGS. 3A and 3C). This threaded hole that is drilled from one side of the articulating arm to the other may be designed to accommodate a bolt or screw that will serve as the connecting point for the controller 102. By manipulation of the controller 102, the articulating arm 103 can move from a position that is at an angle that is 0° relative to the main, arm to a position that is 180° relative to position of the main arm. In an embodiment, at the far end, the articulating arm 103 may contain a tapped threaded hole 303 that is designed to accommodate a threaded rod 302. This threaded rod may allow an extension to be added to the articulating arm 103 if it is needed. Alternatively, the threaded rod 302 may contain a claim (not shown) that may allow the hose to be clamped to the threaded rod 302.

Figure 4C:
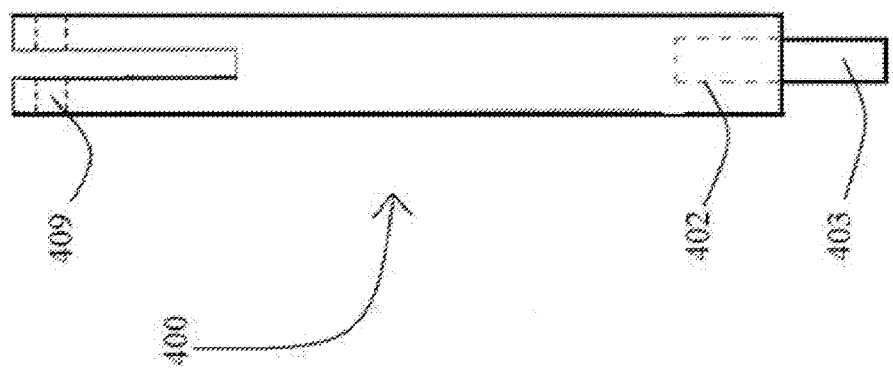
FIG. 4A, FIG. 4B, and FIG. 4C show the front view (FIG. 4A), the side view (FIG. 4B) and back view (FIG. 4C) of a part of the main arm, respectively.
Figure 4B:
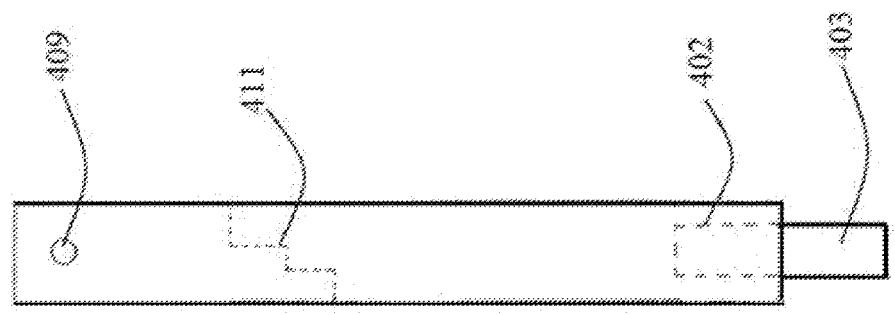
Figure 4A:
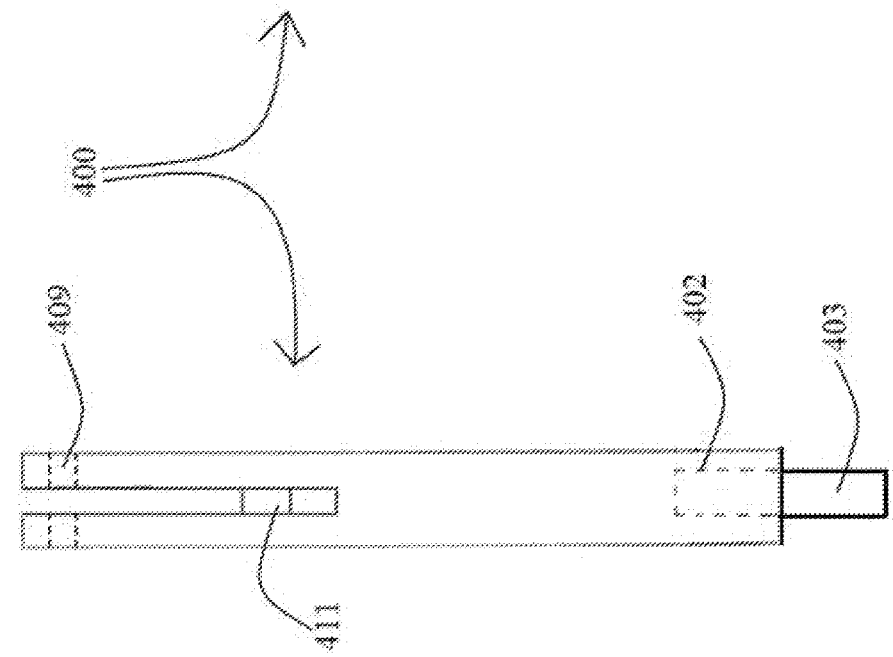

FIGS. 4A, 4B, and 4C show the front view, the side view and back view of a part of the main arm 400, respectively. As described above, hole 409 is aligned with joint 109 from FIG. 3B. Similarly to FIGS. 3A-C, the main arm in FIGS. 4A-C has a threaded hole 402 that allows the insertion of a threaded rod 403. Thus, in one embodiment an additional arm part can be added at the end of part 400 to the threaded rod 403 increasing the length of the main arm 104. In an alternate embodiment, the hole 402 and the threaded rod 403 may not be present, it should be noted that slit 404 is designed to accommodate thin part 304 of the articulating arm 103 with the step like feature 311 of the articulating arm 103 designed to fit in step-like receiving feature 411.

In an embodiment, the main arm and articulating arm is made of a material, that is relatively structurally solid, for example, the main arm and articulating arm may be made of metal, such as steel or iron, wood, a hard plastic, or a hard rubber. In one embodiment, if the main arm and articulating arm is made of hard plastic, that plastic may be one or more members selected from the group consisting of polypropylene, phenol/formaldehyde polymer, a polyvinylchloride polymer, a polycarbonate polymer, a butadiene styrene copolymer, a polycarbonate butadiene styrene copolymer, a polyetherether ketone polymer, a polyarylether ketone polymer, and a clay nanosheet-containing water soluble polymer, or combinations thereof In an embodiment, the hose has a diameter that allows water or a solvent entering and exiting the hose to have sufficient pressure so as to be able to adequately clean the carboy or container in which the apparatus enters. In one embodiment, the hose may be on the order of ½ inch in inner diameter or alternatively, ¼ inch in diameter (inner diameter), or alternatively, ⅜ inch in diameter. It should be understood that the pressure that emanates from water or a solvent leaving the hose can be increased by decreasing the inner diameter of the hose (as long as the water or solvent volume entering the hose does not decrease at a rate greater than the ratio of the diameters). Thus, it is contemplated and therefore within the scope of the invention that inner diameters smaller than ¼ of an inch may be used (for example, inner diameters of 3/16 inch or ⅛ inch are contemplated). In cases, where the pressure is high, the wall of the hose may have to increase in thickness to accommodate that increased pressure.

In an embodiment, the hose is made of a material that can handle relatively high pressures and in an embodiment, may be able to handle solvents other than water. Exemplary solvents that may pass through the hose include bleach, ammonia, detergents, descaling solvents, acids, and/or bases.

In an embodiment, the controller is made of a material that provides sufficient structural rigidity yet is light enough so that it can perform its intended function. In one embodiment, the controller may be made of metal, such as steel or aluminum or a metal alloy that is strong and is not easily deformed. Alternatively, the controller may be made of a hard plastic or rubber that is not easily breakable.

In an embodiment the invention relates to methods of cleaning containers using the apparatus of the present invention, in an embodiment, the method includes the cleaning of carboys that are used for brewing beers. Other methods are contemplated like a method of preventing or diminishing contamination or smell form dirty containers by using the apparatus o the present invention.

In an embodiment, the present invention relates to a spraying apparatus comprising a main arm, an articulating arm, a controller and a hose, said main arm being operationally connected to the articulating arm, said controller being operationally connected to and controlling an amount of articulation by said articulating arm; wherein said articulating arm is able to articulate from an amount that is 0 degrees relative to said main arm to an amount that is about 180 degrees relative to said main arm.

In one variation, the hose has a proximal end and a distal end wherein the proximal end of the hose is clamped on to the main arm and the distal end of the hose is clamped to the for end of the articulating arm.

In one embodiment, the controller at a first end is attached at a connection point on the articulating arm and at a second end is at a position that is proximal to a user of the apparatus. The controller can be manipulated at the proximal end in such a way as to allow the articulating arm to articulate. In one variation, the controller manipulates the articulating arm by a pushing or pulling of the controller, causing the articulating arm to articulate.

In one variation, the connection point comprises a screw or bolt, the screw or bolt attaching to the controller allowing the articulating arm to be articulated.

In one variation, the articulating arm has a near end and a far end, the near end deposed adjacent the main arm and the far end adjacent the distal end of the hose.

In one variation, the connection point on the articulating arm is positioned, about halfway between the near end and the far end of the articulating arm.

In one embodiment, when the articulating arm is in a position that is about 0 degrees relative to said main arm, the apparatus is able to be inserted into the opening of the carboy. The carboy opening may be able to allow passage of the spraying apparatus when the articulating arm has an angle that is between about 0-20 degrees and/or 160-180 degrees relative to the main arm.

In one embodiment, the inner diameter of the hose may be between about ⅛ inch and ½ inches.

In one embodiment, the main arm, the articulating arm, and the controller may be made of steel.

In an embodiment, the present invention relates to a spraying apparatus comprising a main arm, an articulating arm, a controller and a hose, the main arm being operationally connected to the articulating arm, the controller being operationally connected to and controlling an amount of articulation by the articulating arm; wherein the articulating arm is able to articulate from an amount that is 0 degrees relative to the main arm to an amount that is about 180 degrees relative to the main arm, the articulating arm comprising a near end and a far end and the hose comprising a proximal end and a distal end, the near end of the articulating arm being deposed adjacent to the main arm and the far end of the articulating arm being adjacent the distal end of the hose. In one variation, the hose comprises an inner diameter that may be between about 1/16 and ⅝ inches.

In one embodiment, the apparatus comprises a connection point on the articulating arm that is about halfway between the near end and the far end of the articulating arm.

In one variation, the hose has an inner diameter between about 1/32 inch and ¾ inch.

In one embodiment, the present invention relates to a method of cleaning a carboy, said method comprising inserting a spraying apparatus into said, carboy, said spraying apparatus comprising a main arm, an articulating arm, a controller and a hose, said main arm being operationally connected to the articulating arm, said controller being operationally connected to and controlling an amount of articulation by said articulating arm; wherein said articulating arm is able to articulate from an amount that is 0 degrees relative to said main arm to an amount that is about 180 degrees relative to said main arm, said articulating arm comprising a near end and a far end and said hose comprising a proximal end and a distal end, said near end of the articulating arm being deposed adjacent, to the main arm and said far end of the articulating arm being adjacent the distal end of the hose, wherein said spraying apparatus sprays a liquid into the carboy thereby cleaning the carboy.

In one variation of the method, the apparatus sprays water or a solvent into the carboy.

In a variation of the method, the hose comprises an inner diameter that is between about ⅛ and ½ inch.

In one embodiment, the method further comprises ridding the carboy of bacteria. In a variation of the method, the inner upper surface of the carboy can be easily cleaned because the articulating arm is able to attain angles that allow the water solvent or bleach that comes from the hose reach the entire inner surface of the carboy. In one variation of the method, the solvent comprises bleach. In one variation a combination of water and bleach is used. For example, in one embodiment, one might use a teaspoon of bleach with five gallons of water.

It should be understood that the present invention, is not to be limited by the above description. Modifications can be made to the above without departing from the spirit and scope of the invention. It is contemplated and therefore within the scope of the present invention that any feature that is described above can be combined with any other feature that is described above (even if those features are not described together). Moreover, it should be understood that the present invention contemplates and it is therefore within the scope of the invention that any element that is described can be omitted from the apparatus and/or methods of the present invention. In any event, the scope of protection to be afforded is to be determined by the claims which follow and the breadth of interpretation which the law allows.

The invention claimed is:

1. A spraying apparatus comprising a main arm, an articulating arm, a controller and a hose, said main arm being operationally connected to the articulating arm, said controller being operationally connected to and controlling an amount of articulation by said articulating arm; wherein said articulating arm is able to articulate from an amount that is about 0 degrees relative to said main arm to an amount that is about 180 degrees relative to said main arm and wherein said articulating arm comprises a step like feature that is able to accommodate a step like receiving feature on the main arm thereby preventing the articulating arm from going beyond the amount that is about 180 degrees.

2. The apparatus of claim 1, wherein said hose has a proximal end and a distal end wherein said proximal end is clamped on to said main arm and said distal end is clamped to said articulating arm.

3. The apparatus of claim 1, wherein said controller at a first end is attached at a connection point on the articulating arm and at a second end is at a position that is proximal to a user of the apparatus.

4. The apparatus of claim 3, wherein the controller manipulates the articulating arm by a pushing or pulling of the controller.

5. The apparatus of claim 3, wherein the connection point comprises a screw or bolt.

6. The apparatus of claim 2, wherein the articulating arm has a near end and a far end, the near end deposed adjacent the main arm and the far end adjacent the distal end of the hose.

7. The apparatus of claim 6, further comprising a connection point on the articulating arm that is positioned about halfway between the near end and the far end.

8. The apparatus of claim 1, wherein when the articulating arm is in a position that is about 0 degrees relative to said main arm, the apparatus is able to be inserted into a carboy.

9. The apparatus of claim 2, wherein an inner diameter of the hose is between about ⅛ inch and ½ inch.

10. The apparatus of claim 1, wherein the main arm, the articulating arm, and the controller is made of steel.

11. A spraying apparatus comprising a main arm, an articulating arm, a controller and a hose, said main arm being operationally connected to the articulating arm, said controller being operationally connected to and controlling an amount of articulation by said articulating arm; wherein said articulating arm is able to articulate from an amount that is about 0 degrees relative to said main arm to an amount that is about 180 degrees relative to said main arm and wherein said articulating arm comprises a step like feature that is able to accommodate a step like receiving feature on the main arm thereby preventing the articulating arm from going beyond the amount that is about 180 degrees, said articulating arm comprising a near end and a far end and said hose comprising a proximal end and a distal end, said near end of the articulating arm being deposed adjacent to the main arm and said far end of the articulating arm being adjacent the distal end of the hose.

12. The apparatus of claim 11, wherein the hose comprises an inner diameter that is between about ⅛ and ½ inch.

13. The apparatus of claim 11, further comprising a connection point on the articulating arm that is about halfway between the near end and the far end of the articulating arm.

14. The apparatus of claim 13, wherein the hose has an inner diameter between about ⅛ inch and ½ inch.

15. A method of cleaning a carboy, said method comprising inserting a spraying apparatus into said carboy, said spraying apparatus comprising a main arm, an articulating arm, a controller and a hose, said main arm being operationally connected to the articulating arm, said controller being operationally connected to and controlling an amount of articulation by said articulating arm; wherein said articulating arm is able to articulate from an amount that is about 0 degrees relative to said main arm to an amount that is about 180 degrees relative to said main arm and wherein said articulating arm comprises a step like feature that is able to accommodate a step like receiving feature on the main arm thereby preventing the articulating arm from going beyond the amount that is about 180 degrees, said articulating arm comprising a near end and a far end and said hose comprising a proximal end and a distal end, said near end of the articulating arm being deposed adjacent to the main arm and said far end of the articulating arm being adjacent the distal end of the hose, wherein said spraying apparatus sprays a liquid into the carboy thereby cleaning the carboy.

16. The method of claim 15, wherein the apparatus sprays water or a solvent into the carboy.

17. The method of claim 15, wherein the hose comprises an inner diameter that is between about ⅛ and ½ inch.

18. The method of claim 15, wherein said method further comprises ridding the carboy of bacteria.

19. The method of claim 15, wherein an inner upper surface of the carboy can be easily cleaned.

20. The method of claim 18, wherein said method comprises using bleach.

* * * * *